(12) United States Patent
Kato

(10) Patent No.: US 7,367,946 B2
(45) Date of Patent: May 6, 2008

(54) ULTRASONIC DIAGNOSTIC APPARATUS WITH AUTOMATIC MARKING

(75) Inventor: Sei Kato, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 387 days.

(21) Appl. No.: 11/009,985

(22) Filed: Dec. 10, 2004

(65) Prior Publication Data

US 2005/0131293 A1 Jun. 16, 2005

(30) Foreign Application Priority Data

Dec. 11, 2003 (JP) ............................. 2003-413164

(51) Int. Cl.
*A61B 8/00* (2006.01)
(52) U.S. Cl. ...................................... 600/443; 382/128
(58) Field of Classification Search ................ 600/437, 600/443; 382/128
See application file for complete search history.

(56) References Cited

U.S. PATENT DOCUMENTS

| | | | |
|---|---|---|---|
| 5,099,847 A * | 3/1992 | Powers et al. | 600/443 |
| 5,353,354 A * | 10/1994 | Keller et al. | 382/128 |
| 5,582,173 A | 12/1996 | Li | |
| 5,636,631 A | 6/1997 | Waitz et al. | |
| 5,687,200 A | 11/1997 | Berger | |
| 5,976,088 A * | 11/1999 | Urbano et al. | 600/443 |
| 5,993,390 A * | 11/1999 | Savord et al. | 600/437 |
| 6,014,473 A | 1/2000 | Hossack et al. | |
| 6,102,865 A | 8/2000 | Hossack et al. | |
| 6,139,500 A * | 10/2000 | Clark | 600/443 |
| 6,447,450 B1 * | 9/2002 | Olstad | 600/437 |
| 6,503,203 B1 * | 1/2003 | Rafter et al. | 600/458 |
| 6,514,202 B2 | 2/2003 | Grunwald | |
| 6,558,325 B1 * | 5/2003 | Pang et al. | 600/443 |
| 6,673,017 B1 * | 1/2004 | Jackson | 600/437 |
| 6,730,032 B2 * | 5/2004 | Yamauchi | 600/443 |
| 7,175,598 B2 * | 2/2007 | Yoneyama | 600/443 |

FOREIGN PATENT DOCUMENTS

| | | |
|---|---|---|
| JP | 09-201358 | 8/1997 |
| JP | 2000-152931 | 6/2000 |
| JP | 2001-178723 | 7/2001 |
| JP | 2002-065667 | 3/2002 |
| JP | 2002-112254 | 4/2002 |
| JP | 2003-290225 | 10/2003 |

OTHER PUBLICATIONS

Reason for Rejection 2003-413164; 2 pgs.

* cited by examiner

*Primary Examiner*—Ruth S. Smith
*Assistant Examiner*—Jonathan Cwern
(74) *Attorney, Agent, or Firm*—Armstrong Teasdale LLP

(57) ABSTRACT

An ultrasonic diagnostic apparatus includes an image producing section which produces images of time-serial frames of an inspection subject based on echoes of ultrasonic waves emitted to the subject, a marking section which marks certain frame images among the frame images produced by the image producing section, and a cine memory which memorizes data of the frame images produced by the image producing section and the time-serial positions of the frame images marked by the marking section.

20 Claims, 4 Drawing Sheets

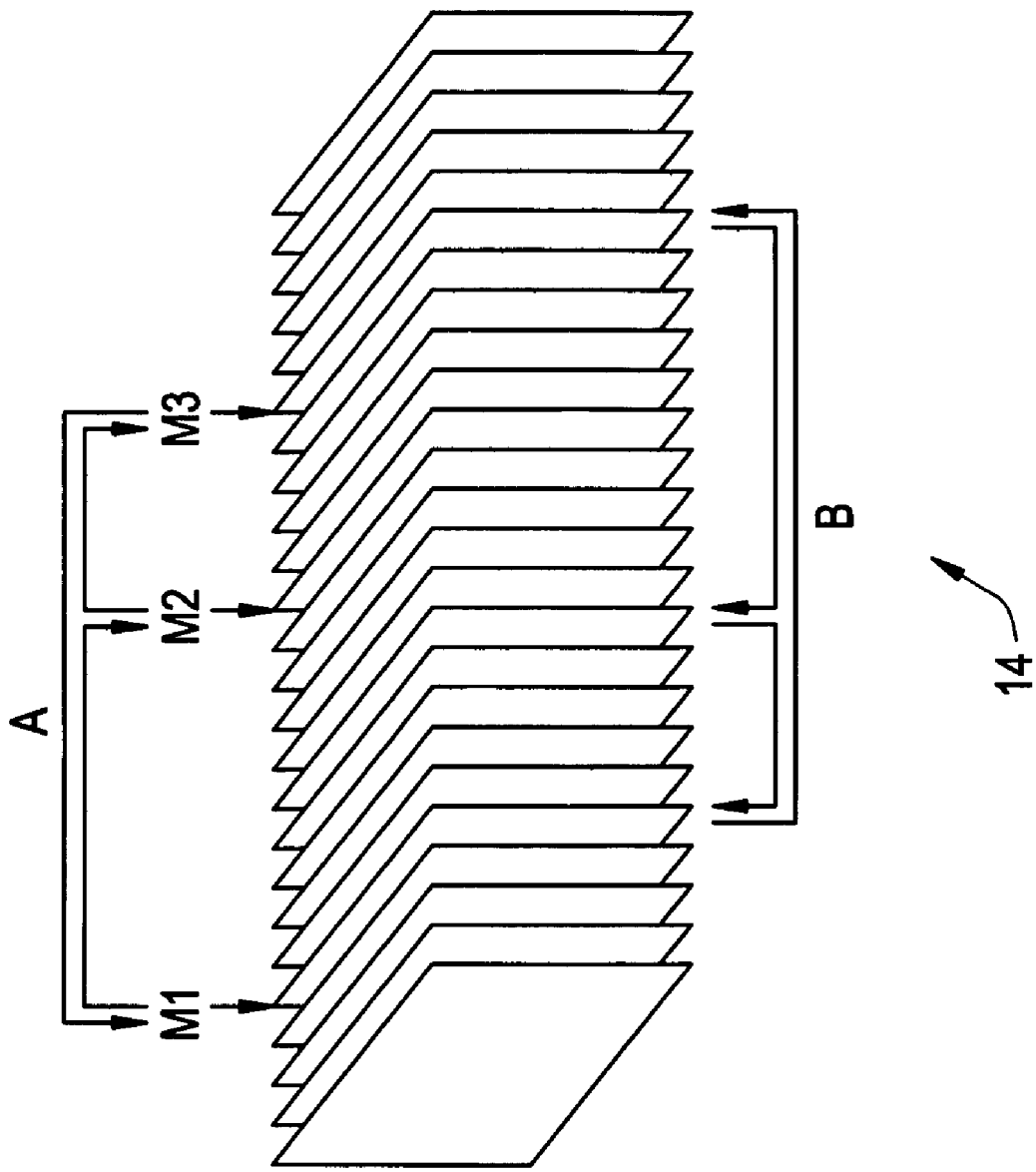

ULTRASONIC DIAGNOSTIC APPARATUS WITH AUTOMATIC MARKING

CROSS REFERENCE TO RELATED APPLICATIONS

This application claims the benefit of Japanese Application No. 2003-413164 filed Dec. 11, 2003.

BACKGROUND OF THE INVENTION

The present invention relates to an ultrasonic diagnostic apparatus.

The ultrasonic diagnostic apparatus is known to used for displaying tomographic images (B-mode images) of an inspection subject by using ultrasonic waves. The ultrasonic diagnostic apparatus, which is capable of readily producing tomographic images on a real-time basis, is used extensively in the medical field for the inspection of a fetus, a heart, etc.

The ultrasonic diagnostic apparatus has various operation modes including B mode, M mode, and D mode. The B mode is mainly used for tomographic imaging of stationary organs of the inspection subject. The M mode, which displays a sonic line of time-serial B-mode images, is used for viewing the motion of a moving part such as a valve of a heart. The D mode, which is based on the Doppler effect of ultrasonic waves reflected by a moving part which causes the echo frequency to shift in proportion to the velocity of movement, is used for measuring the blood flow speed and for imaging a blood stream.

The ultrasonic diagnostic apparatus includes a primary recording device called "cine memory". The cine memory memorizes data of tomographic images of an inspection subject in the form of frames which have been produced consecutively by scanning (for example, refer to Patent Document 1.)

[Patent Document 1] Japanese Unexamined Patent Publication No. 2002-112254

The cine memory is a ring buffer memory having a small storage capacity and is capable of high-speed data writing. The memory stores produced image data of frames until it is full and thereafter stores image data of frames by overwriting the oldest frame with the newest frame sequentially.

After the stop of the scanning operation, image data stored in the cine memory is used for display, and can also be saved in a secondary recording device having a large storage capacity such as a HDD (Hard Disk Drive) unit. Incidentally, a removable medium may be used as the secondary recording device.

When outputting the image data from the cine memory to the HDD unit, not only the image data of the all frames stored in the cine memory can be outputted and saved, but also the image data of frames within an intended range can be saved. Since only a necessary range of frames is saved, unnecessary image data is not displayed at diagnosis of the inspection subject, therefore the diagnosis by the inspector can efficiently be performed. Further, since the image of the unnecessary frame is not stored in the HDD unit, a storage capacity of the HDD unit can be efficiently used.

Conventionally, the operator transfers frame images within a necessary range from the cine memory to the HDD unit by displaying frame images sequentially and setting the start point and end point of the frame range by fast feeding the frames forwardly and reversely many times with an operation device, such as a trackball device or the like.

Since the operator performs awkward operations such as fast feeding the frames forwardly and reversely repeatedly in order to set the necessary range, the operator has to bear a great burden, resulting in a low operational efficiency.

SUMMARY OF THE INVENTION

Therefore, it is an object of the present invention to provide an ultrasonic diagnostic apparatus which is capable of relieving the operator of awkward operations and improving the operational efficiency.

In order to achieve the above objective, the ultrasonic diagnostic apparatus of the present invention comprises an image producing means which produces images of time-serial frames of an inspection subject based on echoes of ultrasonic waves emitted to the subject, a marking means which marks certain frame images among the frame images produced by the image producing means, and a first memory means which memorizes data of the frame images produced by the image producing means and the time-serial positions of the frame images marked by the marking means.

In the inventive ultrasonic diagnostic apparatus, the image producing means produces images of time-serial frames of an inspection subject based on echoes of ultrasonic waves emitted to the subject. The marking means marks certain frame images among the frame images produced by the image producing means. The first memory means memorizes the frame images produced by the image producing means and the time-serial positions of the frame images marked by the marking means.

The inventive ultrasonic diagnostic apparatus is capable of relieving the operator's awkward operations and improving the operational efficiency. Further objects and advantages of the present invention will be apparent from the following description of the preferred embodiments of the invention as illustrated in the accompanying drawings.

BRIEF DESCRIPTION OF THE DRAWINGS

FIG. 4 is a diagram used to explain the manner of saving selectively image data of a certain frame range from the cine memory to the HDD unit.

DETAILED DESCRIPTION OF THE INVENTION

An embodiment of this invention will be explained with reference to the drawings.

Figure 1:
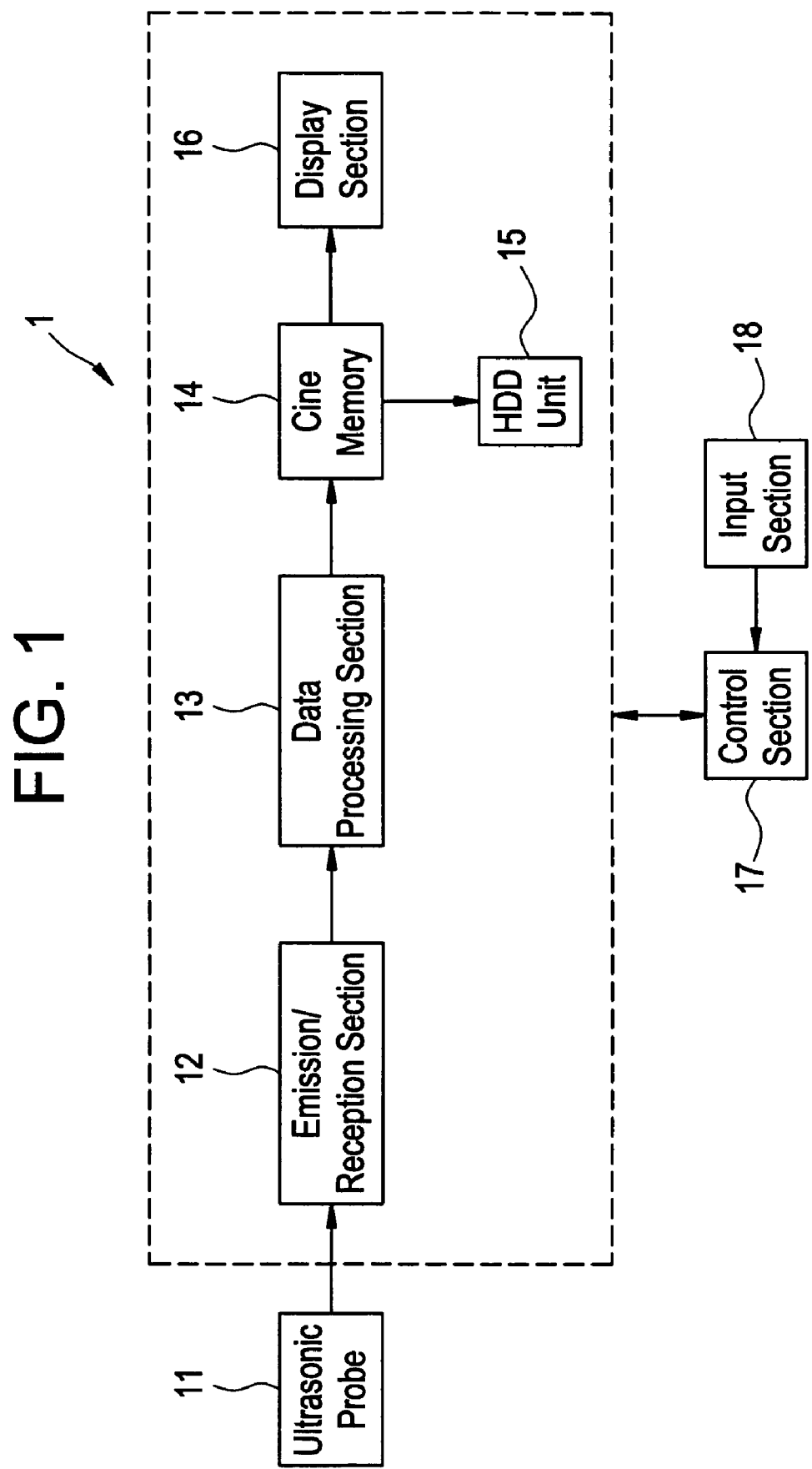
FIG. 1 is a block diagram showing the overall arrangement of the ultrasonic diagnostic apparatus based on an embodiment of this invention.

FIG. 1 shows by block diagram the overall arrangement of the ultrasonic diagnostic apparatus based on an embodiment of this invention.

The ultrasonic diagnostic apparatus 1 includes an ultrasonic probe 11, an ultrasonic wave emission/reception section 12, a data processing section 13, a cine memory 14, a HDD unit 15, a display section 16, a control section 17, and an input section 18.

The cine memory 14 of this embodiment is a derivative of first memory means of this invention. The HDD unit of this embodiment is a derivative of second memory means of this invention. The display section 16 of this embodiment is a derivative of display means of this invention. The input section 18 of this embodiment is a derivative of input means of this invention.

The ultrasonic probe 11 includes an array of vibration elements (not shown). Each vibration element is formed of piezoelectric material including PZT (titanic acid zirconic acid lead) and ceramics. The ultrasonic probe 11, which is manipulated by the operator to come in contact with an inspection subject, operates in accordance with the command from the control section 17 to emit ultrasonic waves into the inspection subject in response to the signals provided by the emission/reception section 12 and to detect ultrasonic echoes from inside of the inspection subject. The ultrasonic probe 11 has a sensor (not shown) for detecting the probe position.

The emission/reception section 12 is connected to the ultrasonic probe 11 and operates in accordance with the command of the control section 17. The emission/reception section 12 supplied the drive signals, by which ultrasonic waves are released into the subject, and outputs to the data processing section 13 the reception signals, which are based on echoes of ultrasonic waves detected by the probe 11. Specifically, the emission/reception section 12 applies the drive signals to the ultrasonic probe 11 repeatedly at certain time intervals while varying the direction of sonic beam in steps. The emission/reception section 12 implements the amplifying, delaying, and summing processes for the echo signals received by the probe 11 to produce reception signals.

The data processing section 13 implements various data processings in accordance with the commands from the control section 17.

Figure 2:
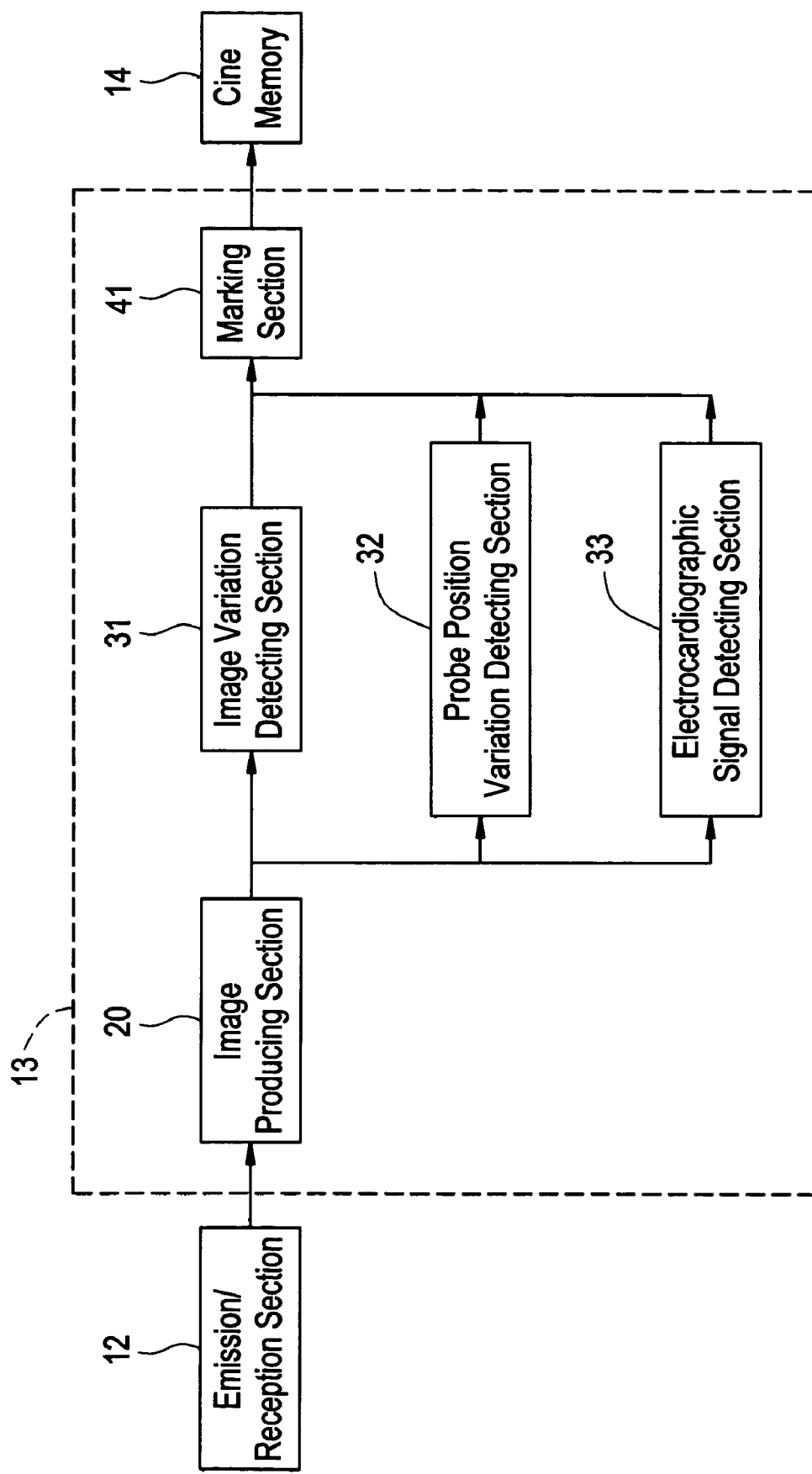
FIG. 2 is a block diagram showing the arrangement of the data processing section of the ultrasonic diagnostic apparatus of this embodiment.

FIG. 2 shows by block diagram the arrangement of the data processing section 13.

The data processing section 13 includes an image producing section 20, an image variation detecting section 31, a probe position variation detecting section 32, an electrocardiographic signal detecting section 33, and a marking section 41.

The image producing section 20 of this embodiment is a derivative of image producing means of this invention. The image variation detecting section 31 of this embodiment is a derivative of image variation detecting means of this invention. The probe position variation detecting section 32 of this embodiment is a derivative of probe position variation detecting means of this invention. The electrocardiographic signal detecting section 33 of this embodiment is a derivative of electrocardiographic signal detecting means of this invention. The marking section 41 of this embodiment is a derivative of marking means of this invention.

The image producing section 20 is connected to the emission/reception section 12 and operates in accordance with the command from the control section 17. The image producing section 20 processes the reception signal output from the emission/reception section 12, thereby producing a time-serial frame image of the inspection subject, and outputs the produced image data into the cine memory 14. The image producing section 20 has, for example, a logarithmic amplifying section (not shown), an envelope detecting section (not shown), and a B-mode image producing section (not shown) that produces a B-mode image. Specifically, the image producing section 20 uses the logarithmic amplifying section to implement logarithmic amplification of the reception signal provided by the emission/reception section 12, uses the envelope detecting section to detect the envelope of the signal, and uses the B-mode image producing section to produce a frame image.

The image variation detecting section 31 operates in accordance with the command of the control section 17 to detect a time-wise change of the time-serial frame images produced by the image producing section 20 and to output the detection result to the marking section 41.

The probe position variation detecting section 32 operates in accordance with the command of the control section 17 to detect a change in position of the ultrasonic probe 11 and output the detection result to the marking section 41.

The electrocardiographic signal detecting section 33 operates in accordance with the command of the control section 17 to detect the electrocardiographic signal of the inspection subject and output the detection result to the marking section 41.

The marking section 41 operates in accordance with the command of the control section 17 to mark certain frame images among the frame images produced by the image producing section 20 as will be explained in detail in the following.

For example, the marking section 41 marks frame images in accordance with the instruction entered by the operator on the input section 18. The marking section 41 marks frame images which are specified by the operator by use of a marking instruction input section 51 of input section 18 which will be explained later. In case the operator instructs on the input section 18 the alteration of a scanning condition such as the scanning mode, FOV (field of view), focal point, acoustic output level, emission waveform, frame rate or scanning area (imaging angle), the marking section 41 marks automatically the frame images in accordance with the instruction. In this embodiment, at the time of marking of a frame image by the marking section 41, a mark of a preset color is displayed at a certain position of display on the display section 16.

The marking section 41 also marks frame images produced at certain, predetermined time intervals by the image producing section 20. Specifically, for example, the marking section 41 marks the frame images produced at one second intervals among the plurality of frame images produced by the image producing section 20. Also in this case, a mark is displayed at a certain position of display on the display section 16, but in a color which is set differently from the case mentioned previously.

The marking section 41 also marks the frame images which are produced by the image producing section 20 upon expiration of a certain, predetermined time length. Specifically, for example, the marking section 41 marks the frame images, from the plurality of frame images produced by the image producing section, that were produced 10 seconds or more after the start of a scan. A mark in a color which is set differently from the cases mentioned previously is displayed on the display section 16.

The marking section 41 also marks frame images in response to a change of time-serial frame images detected by the image variation detecting section 31. Specifically, for example, the marking section 41 compares the rate of change of time-serial frame images detected by the image variation detecting section 31 with a threshold value and marks frame images based on the comparison result. For example, the marking section 41 marks frame images having a rate of change of image intensity that is not within a preset range for the rate of change of image intensity. Specifically, the marking section 41 calculates correlation factors between frame images and marks frame images in case the correlation factors are below the threshold value. A mark in a color which is set differently from the cases mentioned previously is displayed on the display section 16. For example, frame images having large rates of change, such as those frame images at the start and end of a scan, are marked.

The marking section 41 also marks frame images in response to a change in position of the ultrasonic probe 11 as detected by the probe position variation detecting section 32. Specifically, for example, the marking section 41 compares the rate of positional change of the ultrasonic probe 11 with a threshold value and marks frame images based on the comparison result. For example, the marking section 41 marks frame images having a rate of change of probe position that is not within a preset range for rate of change of probe position. Specifically, the marking section 41 marks frame images when the probe 11 has moved into a preset area. A mark in a color which is set differently from the cases mentioned previously is displayed on the display section 16. For example, a frame image on which the ultrasonic probe 11 has moved by a specified distance, has stopped moving, or has reached a specified position is marked.

The marking section 41 also marks frame images in response to an electrocardiographic signal of the inspection subject as detected by the electrocardiographic signal detecting section 33. For example, the marking section 41 marks frame images in response to the R wave of electrocardiographic signal detected by the electrocardiographic signal detecting section 33. Specifically, the marking section 41 marks frame images having a time interval of the R wave of electrocardiographic signal that is not within a preset range of time intervals. A mark in a color which is set differently from the cases mentioned previously is displayed on the display section 16. For example, frame images are marked in response to abnormal heart beats or in synchronism with the heart beat.

In this manner, the marking section 41 operates to mark frame images on a real-time basis at the imaging of inspection subject based on the scanning of subject by the image producing section 20. The marking section 41 marks frame images which have been memorized in the cine memory 14 following the scanning. In this embodiment, the marking section 41 marks frame images based on the operator's instruction, based on the time interval, based on the expiration time, based on the time-wise change of frame images, based on the positional change of the ultrasonic probe 11 and based on the electrocardiographic signal, and displays marks in corresponding colors on these frame images as described above.

The cine memory 14, which is connected to the data processing section 13, operates in accordance with the command from the control section 17 to store data of the frame images, which have been produced by the image producing section 20 of the data processing section 13. The time-serial positions of the frame images which have been marked by the marking section 41 of the data processing section 13 are also stored in the cine memory 14. The cine memory 14, which is a ring buffer for example, sequentially stores data of frame images until the cine memory 14 is full and thereafter stores frame image data by overwriting the oldest frame with the newest frame sequentially.

The HDD unit 15 operates in accordance with the command from the control section 17 to store frame image data from the cine memory 14. The HDD unit 15 has a larger storage capacity than the cine memory 14. The HDD unit 15 also stores data of frame images based on the time-serial positions of frame images selected by a mark selecting input section 52 of input section 18, which will be explained later.

The display section 16 includes a color graphic display unit and a digital scan converter (DSC), for example. The display section 16 is connected to the cine memory 14 and operates in accordance with the command from the control section 17 to convert data of a frame image read out of the cine memory 14 into a video signal with the DSC and displays a reproduced image on the screen of graphic display unit.

The control section 17 is a combination of a computer and programs. The control section 17 is connected with the ultrasonic probe 11, emission/reception section 12, data processing section 13, cine memory 14, HDD unit 15 and display section 16, and it operates in accordance with the commands from the input section 18 to issue control signals to the individual sections, thereby controlling their operations.

The input section 18 includes a keyboard, a touch-panel, a trackball device, a foot switch, and a voice input device. The input section 18 is used by the operator to enter instructions, and it releases a command to the control section 17 in response to the entered instruction.

Figure 3:
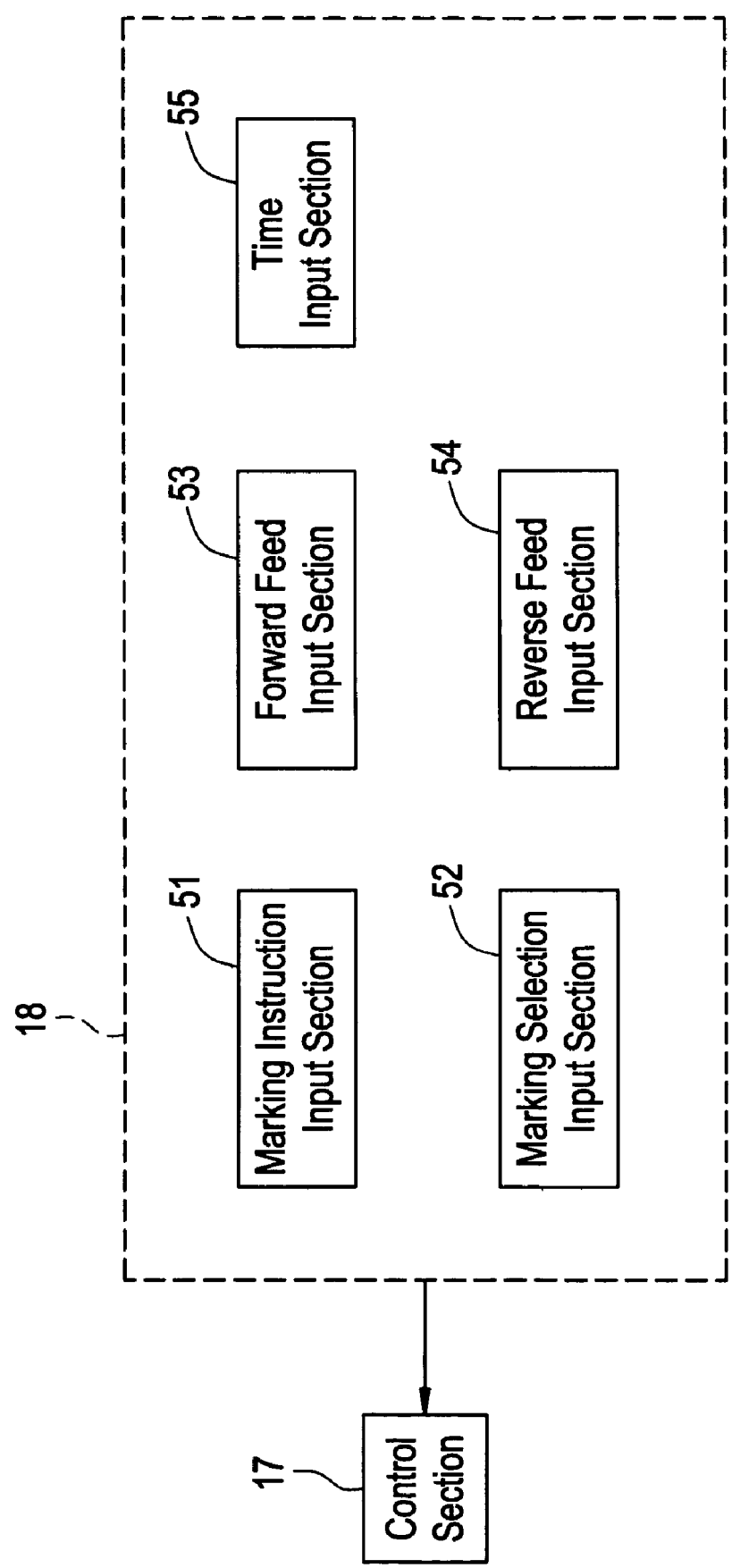
FIG. 3 is a block diagram showing the arrangement of the input section of the ultrasonic diagnostic apparatus of this embodiment.

FIG. 3 shows by block diagram the arrangement of the input section 18.

As shown in FIG. 3, the input section 18 includes a marking instruction input section 51, a marking selection input section 52, a forward feed input section 53, a reverse feed input section 54, and a time input section 55.

The marking instruction input section 51 of this embodiment is a derivative of marking instruction means of this invention. The marking selection input section 52 of this embodiment is a derivative of marking selection means of this invention. The forward feed input section 53 of this embodiment is a derivative of forward feed input means of this invention. The reverse feed input section 54 of this embodiment is a derivative of reverse feed input means of this invention. The time input section 55 of this embodiment is a derivative of time input means of this invention.

The marking instruction input section 51 is used by the operator to enter the instruction of marking to be implemented by the marking section 41. For example, the operator depresses a certain key on the keyboard of the input section 18 to enter to the instruction input section 51 the instruction of marking by the marking section 41. The marking section 41 marks the frame images instructed by the marking instruction input section 51.

The marking selection input section 52 is used by the operator to enter selected time-serial positions of frame images that have been marked by the marking section 41 and memorized in the cine memory 14. For example, the operator depresses a certain key on the keyboard of the input section 18 to enter to the marking selection input section 52 the instruction for selecting time-serial positions of frame images memorized in the cine memory 14. Data of frame images memorized in the cine memory 14 is outputted in accordance with the time-serial positions selected by the marking selection input section 52. The selected frame images are saved in the HDD unit 15. For example, the operator uses the marking selection input section 52 to enter a starting position and ending position of a range of time-serial frame images that have been marked by the marking section 41 and memorized in the cine memory 14. Data of frame images within the selected range is outputted from the cine memory 14 and saved in the HDD unit 15.

The forward feed input section 53 is used by the operator to enter the instruction of forward feed of the time-serial frame images which have been marked by the marking section 41 and memorized in the cine memory 14. For example, the operator depresses a certain key on the keyboard of the input section 18 to enter to the forward feed input section 53 the instruction of forward feed of the frame images memorized in the cine memory 14. At this time, the display section 16 operates based on the instruction entered to the forward feed input section 53 to display forwardly the marked frame images memorized in the cine memory 14. The forward feed input section 53 feeds down to the last of the time-serial marked frames, and thereafter returns to the first of the time-serial marked frames.

The reverse feed input section 54 is used by the operator to enter the instruction of reverse feed of the time-serial frame images which have been marked by the marking section 41 and memorized in the cine memory 14. For example, the operator depresses a certain key on the keyboard of the input section 18 to enter to the reverse feed input section 54 the instruction of reverse feed of the frame images memorized in the cine memory 14. At this time, the display section 16 operates based on the instruction entered to the reverse feed input section 54 to display reversely the marked frame images memorized in the cine memory 14. The reverse feed input section 54 feeds up to the first of the time-serial marked frames, and thereafter returns to the last of the time-serial marked frames.

The time input section 55 is used by the operator to enter the instruction of a time length in case the marking section 41 marks frame images at certain time intervals or on expiration of a certain time length. For example, the operator depresses a certain key on the keyboard of the input section 18 to enter the instruction of a time length to the time input section 55. The time input section 55 operates in accordance with the instructed time length to mark frame images at the time intervals or on expiration of the time length.

Next, the manner of ultrasonic imaging by use of the ultrasonic diagnostic apparatus of this embodiment will be explained.

The operator puts the ultrasonic probe 11 to a portion of the inspection subject to be imaged. The operator operates the input section 18 to select a mode of imaging, e.g., B mode. In B-mode imaging, the emission/reception section 12 scans the inside of subject and receives echoes with the ultrasonic probe 11, and outputs the reception signals which are derived from the echoes to the data processing section 13.

The data processing section 13 operates on its image producing section 20 to implement the logarithmic amplification for the reception signals with the logarithmic amplifying unit and implement the envelope detection with the envelope detecting unit, thereby producing the B-mode images of time-serial frames, and outputs image data to the cine memory 14. The display section 16 converts data of a frame image read out of the cine memory 14 into a video signal with the DSC, and displays the reproduced image on the screen of graphic display unit on a real-time basis.

At the time of producing B-mode images of the subject by the image producing section 20 based on the ultrasonic scanning of the subject, the marking section 41 is used to mark certain frame images on a real-time basis among the frame images produced by the image producing section 20.

For example, the marking section 41 is used to mark frame images in accordance with the operator's instruction entered on the input section 18. Specifically, for example, with the marking instruction input section 51 of the input section 18 being used, the marking section 41 marks the frame images specified by the operator. At the emission and reception of ultrasonic waves, the marking section 41 marks automatically the frame images in response to the entry of operator's instruction on the input section 18 for the alteration of a scanning condition such as the scanning mode, FOV (field of view), focal point, acoustic output level, emission waveform, frame rate, or imaging angle.

For example, the marking section 41 is used to mark the frame images which are produced by the image producing section 20 at preset time intervals or on expiration of a preset time length. With the time input section 55 being used, the marking section 41 marks the frame images in accordance with the time length entered by the operator.

For example, the marking section 41 is used to mark frame images in response to a time-wise change of frame images detected by the image variation detecting section 31. The marking section 41 is used to mark frame images in response to a positional change of the ultrasonic probe 11 detected by the probe position variation detecting section 32. The marking section 41 is used to mark frame images in response to an electrocardiographic signal of the inspection subject detected by the electrocardiographic signal detecting section 33.

Data of frame images produced by the image producing section 20 of the data processing section 13 and the time-serial positions of the frame images marked by the marking section 41 of the data processing section 13 are memorized in the cine memory 14. Data of frame images produced by the image producing section 20 of the data processing section 13 is memorized sequentially in the cine memory 14 until it is full and thereafter memorized such that the oldest frame is overwritten by the newest frame sequentially.

After the scanning operation, data of frame images memorized in the cine memory 14 is used for display repeatedly. Data of frame images memorized in the cine memory 14 is saved in the HDD unit 15 having a large storage capacity and used later arbitrarily. In this case, image data of all frames or only image data of frames of a specified range is saved in the HDD unit.

FIG. 4 explains the manner of selecting frames of a certain range out of the frame images memorized in the cine memory 14 and saving data of the selected frame image in the HDD unit 15. The figure shows 25 time-serial frames memorized in the cine memory 14. The figure also shows that the fifth and 15th frames are marked with a first mark M1 and second mark M2, respectively, by the marking section 41 in accordance with the operator's instruction entered to the marking instruction input section 51. The figure also shows that the 20th frame is marked with a third mark M3 by the marking section 41 in response to a change of image detected by the image variation detecting section 31.

For selecting frames of a certain range out of the frame images memorized in the cine memory 14, the marking selection input section 52 is used. For example, the operator sets a certain range of frames by using the marking selection input section 52 to enter time-serial positions of frame images which have been marked and memorized in the cine memory 14. Specifically, the operator selects the first mark M1 and third mark M3 by using the marking selection input section 52, thereby setting the range from the fifth frame to the 20th frame. Image data of the selected frame range is read out of the cine memory 14 and saved in the HDD unit 15.

At the selection of frames of a certain range by use of the marking selection input section 52, the forward feed input section 53 and reverse feed input section 54 may be used. Specifically, the operator uses the forward feed input section 53 or reverse feed input section 54 to feed the marked frame images forwardly or reversely as shown by the arrows A and B in FIG. 4, thereby displaying these frame images on the display section 16. The operator selects a certain range of frames by using the marking selection input section 52, while confirming the frame images displayed by use of the forward feed input section 53 or reverse feed input section 54, and saves the image data of the selected frame range from the cine memory 14 to the HDD unit 15.

As described above, in this embodiment, the image producing section 20 produces images of time-serial frames of an inspection subject based on echoes of ultrasonic waves emitted to the subject. The marking section 41 marks certain frame images among the frame images produced by the image producing section 20. The cine memory 14 memorizes data of the frame images produced by the image producing section 20 and the time-serial positions of the frame images marked by the marking section 41. The operator uses the marking selection input section 52 to enter selectively time-serial positions of frame images which have been marked by the marking section 41 and memorized in the cine memory 14. Data of the frame images is read out of the cine memory 14 in accordance with the time-serial positions of the frames selected by the marking selection input section 52, and saved in the HDD unit 15. This embodiment is operative to mark and memorize certain frame images among the frame images, and save image data of the marked frames selectively in the HDD unit 15. In consequence, the conventional awkward operations for browsing all frames can be relieved and the operational efficiency can be improved.

In this embodiment, the operator enters instructions into the input section 18. The marking section 41 marks certain frame images in accordance with the operator's instruction entered on the input section 18. At the emission and reception of ultrasonic waves, the marking section 41 marks automatically the frame images in response to the entry of operator's instruction on the input section 18 for the alteration of a scanning condition. Owing to this automatic marking, the awkward operations can be relieved and the operational efficiency can be improved.

In this embodiment, the input section 18 includes the marking instruction input section 51 for the entry of operator's marking instruction to the marking section 41. In consequence, the operator is allowed to mark intended frame images, and the awkward operations can be relieved and the operational efficiency can be improved.

In this embodiment, the input section 18 includes the forward feed input section 53 which is used by the operator to instruct the forward feed of the marked frame images and the reverse feed input section 54 which is used by the operator to instruct the reverse feed of the marked frames images. The display section 16 displays sequentially the marked frame images memorized in the cine memory 14 in response to the operator's instruction entered to the forward feed input section 53 or reverse feed input section 54. The forward feed input section 53 feeds down to the last of the time-serial marked frames, and thereafter returns to the first of the time-serial marked frames. The reverse feed input section 54 feeds up to the first of the time-serial marked frames, and thereafter returns to the last of the time-serial marked frames. In this manner, the operator can view marked frames arbitrarily and easily, whereby the awkward operations can be relieved and the operational efficiency can be improved.

In this embodiment, the marking section 41 is used to mark the frame images which are produced by the scanning of the image producing section 20 at certain time intervals. The marking section 41 is used to mark the frame images which are produced by the scanning of the image producing section 20 on expiration of a certain time length. The input section 18 includes the time input section 55 used by the operator to instruct a certain time length, in accordance with which the marking section 41 marks the relevant frame images. Owing to this automatic marking of frame images based on the intended timing condition, the awkward operations can be relieved and the operational efficiency can be improved.

This embodiment includes the image variation detecting section 31 which detects a time-wise change in the time-serial frame images produced by the image producing section 20, and the marking section 41 marks frame images in response to a change of image detected by the image variation detecting section 31. Owing to this automatic marking of frame images in correspondence to time-wise changes, the awkward operations can be relieved and the operational efficiency can be improved.

This embodiment includes the probe position variation detecting section 32 which detects a change in position of the ultrasonic probe 11, and the marking section 41 marks frame images in response to a change of probe position detected by the probe position variation detecting section 32. Owing to this automatic marking of frame images in correspondence to changes of probe position, the awkward operations can be relieved and the operational efficiency can be improved.

This embodiment includes the electrocardiographic signal detecting section 33 which detects the electrocardiographic signal of the inspection subject, and the marking section 41 marks frame images in response to the electrocardiographic signal detected by the electrocardiographic signal detecting section 33. Owing to this automatic marking of frame images in correspondence to electrocardiographic signals, the awkward operations can be relieved and the operational efficiency can be improved.

The present invention is not confined to the foregoing embodiment, but various variants can be adopted for practicing.

For example, the forward feed input means and reverse feed input means may be designed to feed frame images distinctively for the frame images marked by the marking section based on the operator's instruction and based on other events than the entry of operator's instruction.

Different from the foregoing embodiment, in which the marking means marks frame images based on the operator's instruction, the time interval, the expiration time, the time-wise change of frame image, the positional change of the ultrasonic probe 11, and the electrocardiographic signal, the marking means may mark frame images based on only any one of these events.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic diagnostic apparatus comprising:
   an image producing device which produces a plurality of time-serial frame images of an inspection subject based on echoes of ultrasonic waves emitted to said inspection subject;
   a marking device which automatically marks at least one frame image from among the plurality of produced frame images based on an operator instruction, wherein the marking indicates that the at least one frame image includes a predetermined property designated by the operator instruction; and a first memory device which stores the plurality of produced frame images including at least one marked frame image and at least one unmarked frame image, wherein a time-serial position of the at least one marked frame image is stored in said first memory device.

2. An ultrasonic diagnostic apparatus according to claim 1, wherein said marking device marks the at least one frame image at a time of imaging said inspection subject by said producing device.

3. An ultrasonic diagnostic apparatus according to claim 1 further comprising an input device for entering the operator instruction.

4. An ultrasonic diagnostic apparatus according to claim 3, wherein said marking device marks the at least one frame image in response to the operator instruction entered on said input device.

5. An ultrasonic diagnostic apparatus according to claim 3, wherein said input device includes a marking instruction device for entering a marking instruction.

6. An ultrasonic diagnostic apparatus according to claim 5, wherein said marking instruction device transmits the marking instruction to said marking device.

7. An ultrasonic diagnostic apparatus according to claim 3, wherein said input device comprises a marking selection device for entering a selected time-serial position of a marked frame image stored in said first memory device.

8. An ultrasonic diagnostic apparatus according to claim 3 further comprising a display device which displays the frame images produced by said image producing device, said input device comprises a forward feed input device for entering an instruction to forward feed the time-serial marked frame images stored in said first memory device, said display device displaying, the marked frame images stored in said first memory device according to the forward feed instruction.

9. An ultrasonic diagnostic apparatus according to claim 8, wherein said forward feed input device feeds down to a last of the time-serial marked frames, and thereafter returns to a first of the time-serial marked frames.

10. An ultrasonic diagnostic apparatus according to claim 8, wherein said input device comprises a reverse feed input device for entering an instruction to reverse feed the time-serial marked frame images stored in said first memory device, said display device displaying the marked frame images stored in said first memory device according to the reverse feed instruction.

11. An ultrasonic diagnostic apparatus according to claim 10, wherein said reverse feed input device feeds up to a first of the time-serial marked frames, and thereafter returns to a last of the time-serial marked frames.

12. An ultrasonic diagnostic apparatus according to claim 3, wherein said input device comprises a time input device for entering an instruction of a time length.

13. An ultrasonic diagnostic apparatus according to claim 1 further comprising a second memory device for storing a range of frame images from among the plurality of frame images stored in said first memory device, said second memory device storing the range of frame images based on a time-serial position of at least two marked frame images.

14. An ultrasonic diagnostic apparatus according to claim 1, wherein said marking device marks the frame images produced by said image producing device at selected time intervals.

15. An ultrasonic diagnostic apparatus according to claim 1, wherein said marking device marks the frame images which are produced by said image producing device upon expiration of a selected time length.

16. An ultrasonic diagnostic apparatus according to claim 1 further comprising an image variation detecting device which detects a time-wise change of the produced time-serial frame images, said marking device marks stored frame images in response to a change of image detected by said image variation detecting device.

17. An ultrasonic diagnostic apparatus according to claim 1 configured to be coupled to an ultrasonic probe which emits ultrasonic waves to said inspection subject and receives echoes of the ultrasonic waves from said inspection subject, said ultrasonic diagnostic apparatus further comprising:
a probe position variation detecting device which detects a change in a position of said probe, wherein said marking device marks stored frame images based on the positional change of said ultrasonic probe detected by said probe position variation detecting device.

18. An ultrasonic diagnostic apparatus according to claim 1 further comprising:
an electrocardiographic signal detecting device which detects an electrocardiographic signal of said inspection subject, wherein said marking device marks stored frame images based on the electrocardiographic signal detected by said electrocardiographic signal detecting device.

19. A method of generating ultrasonic data using an ultrasonic diagnostic apparatus including at least an image producing device, a marking device, and a first memory device, said method comprising:
producing a plurality of time-serial frame images using the image producing device;
entering a marking instruction into the ultrasonic diagnostic apparatus, wherein the marking instruction designates a predetermined image property;
automatically marking at least one of the produced frame images using the marking device and the entered marking instruction such that the at least one marked frame image includes the predetermined image property;
storing the plurality of time-serial frame images in the first memory device, wherein the plurality of stored frame images includes the at least one marked frame image and at least one unmarked frame image; and
storing a time-serial position of the at least one marked frame image in the first memory device.

20. A method according to claim 19 further comprising:
transferring a range of frame images, based on stored time-serial positions of at least two marked frames, to a second memory device; and
storing the transferred range of frame images in the second memory device.

* * * * *